United States Patent [19]

Wooff, Jr.

[11] 4,344,667
[45] Aug. 17, 1982

[54] INTEGRATED BEAM SPLITTER AND ADJUSTABLE LIGHT INTENSITY CONTROL ADAPTER

[75] Inventor: Edward A. Wooff, Jr., Ventura, Calif.

[73] Assignee: Circon Corporation, Santa Barbara, Calif.

[21] Appl. No.: 154,874

[22] Filed: May 30, 1980

[51] Int. Cl.³ .......................... G02B 7/00; G02B 27/10
[52] U.S. Cl. ...................................... 350/80; 350/173; 354/62; 358/98
[58] Field of Search ................... 350/173, 171, 33, 19, 350/17, 80, 69; 354/62, 79; 358/98; 128/4, 6

[56] References Cited

U.S. PATENT DOCUMENTS 4,192,591 3/1980 Yobaccio ............................ 354/62
4,248,213 2/1981 Landre ................................ 358/98

FOREIGN PATENT DOCUMENTS 2009642 9/1971 Fed. Rep. of Germany ........ 354/62

Primary Examiner—Jon W. Henry
Attorney, Agent, or Firm—Daniel J. Meaney, Jr.

[57] ABSTRACT

An integrated beam splitter and adjustable light intensity control adapter including a housing having a plurality of hollowed-out areas with openings from the interior thereof to the housing exterior, a connecting adapter to couple an optical device producing an optical image to the housing wherein the optical image passes through the openings within the housing, a viewing means coupled to the housing to enable a viewer to observe the optical image, a beam splitter positioned within the housing in one hollowed-out area to receive the optical image and pass a portion of the optical image along one optical path to the eyepiece and the remainder of the optical image along a second optical path to an optical system including a beam splitter and prism which deflect the remainder of the optical image into a second hollowed-out area within the housing, a light intensity control means positioned along the second optical path between the prism and an aperture extending from the second hollowed-out area to the exterior of the housing and a coupling means for attaching a video camera recording means, is shown.

12 Claims, 6 Drawing Figures

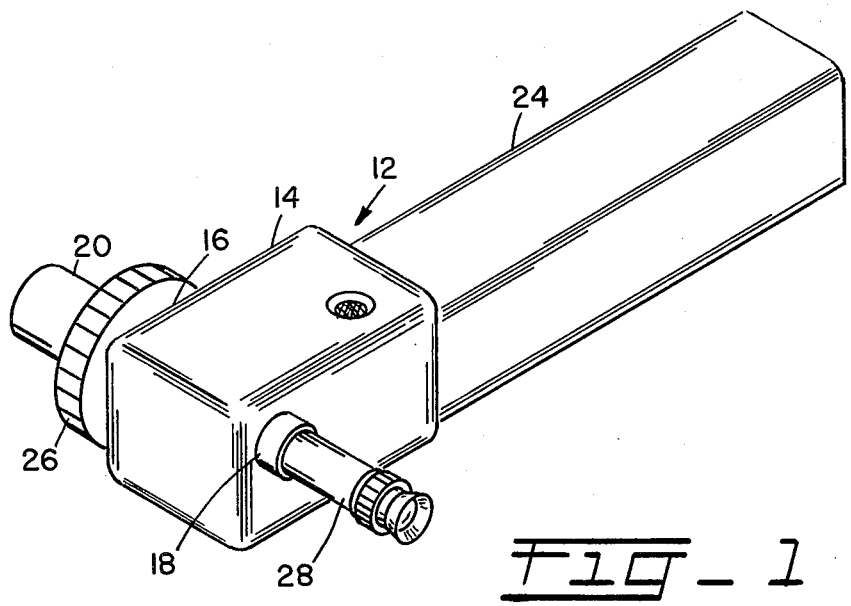
Fig_1
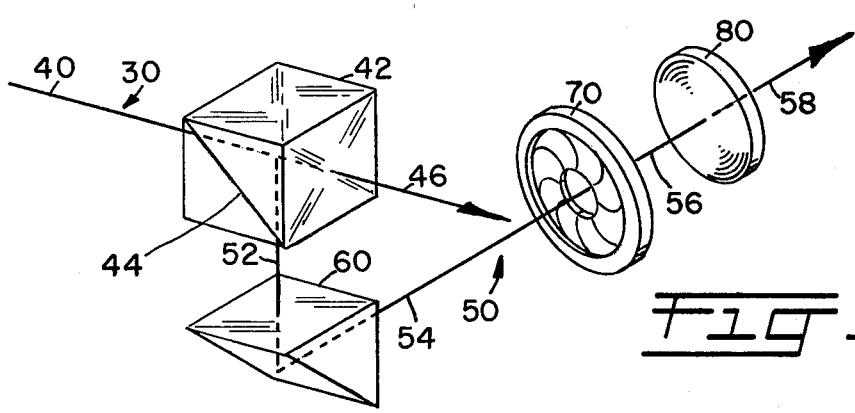
Fig_2
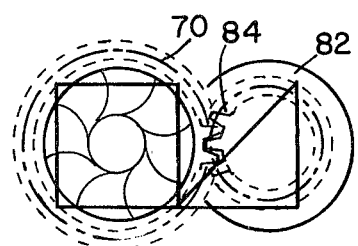
Fig_3
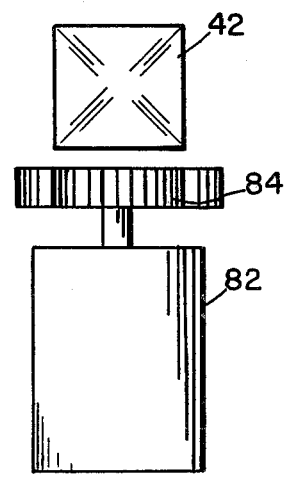
Fig_4

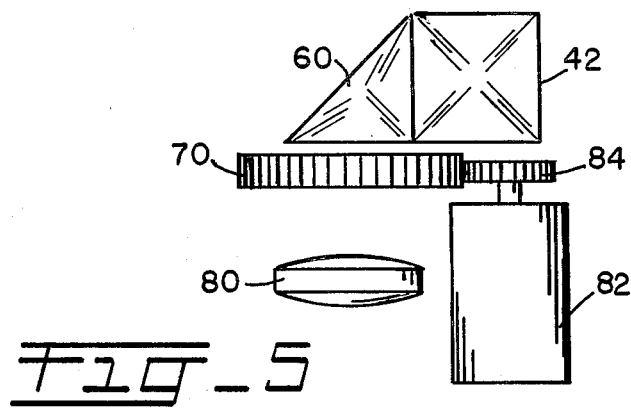
Fig_5
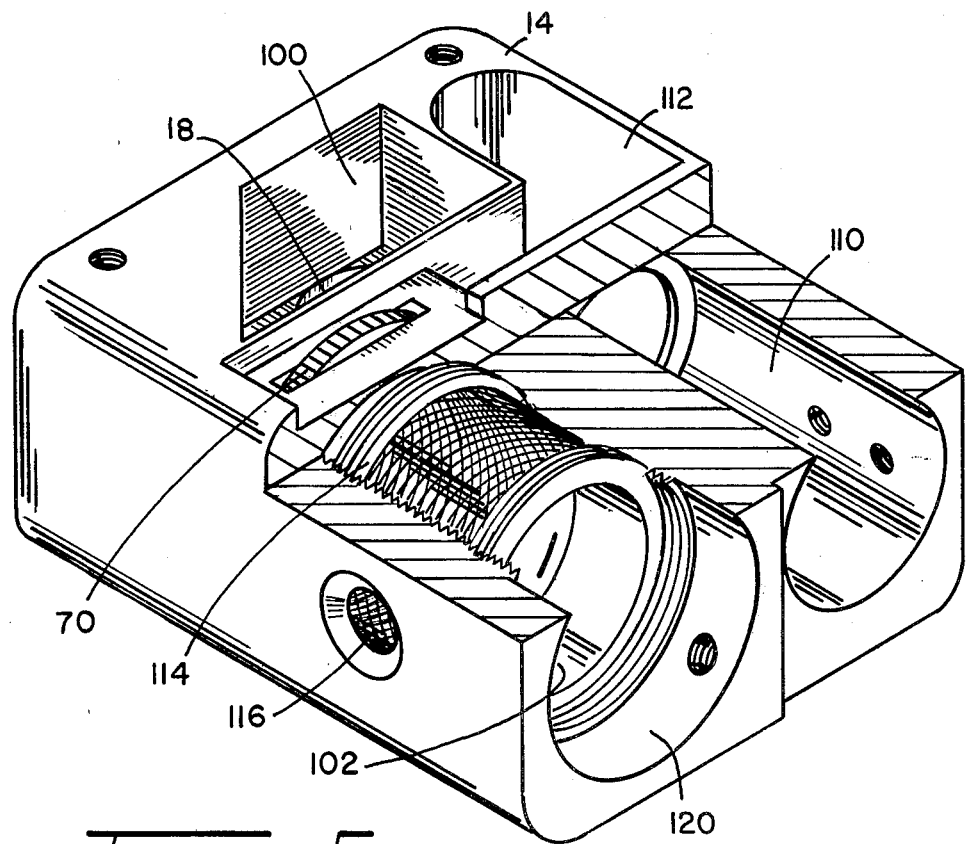
Fig_6

INTEGRATED BEAM SPLITTER AND ADJUSTABLE LIGHT INTENSITY CONTROL ADAPTER

BACKGROUND OF THE INVENTION

1. Field of the Invention

This invention relates to an integrated beam splitter and adjustable light intensity control adapter and more particularly to an adapter including an attachment means for having an optical device which produces an optical image connected to one opening and a viewing means to enable a user to observe the image and a separate attachment for a video camera recording means to record the optical image from the optical device. An adjustable iris controls the intensity of the optical image received by the video recording means.

2. Disclosure of the Prior Art

It is known in the prior art to utilize a beam splitter in combination with a viewing means and a video camera recording means. Also, use of an iris or other light intensity controlling means are known in the prior art. One such system is sold by the assignee of the present invention which is known as an "Endo Video Beam Splitter". This present device is useful but has relatively long optical paths and is used primarily in medical and surgical applications.

Beam splitters are used in the medical industry in cooperation with optical devices used primarily in surgical applications wherein a second observer or a recording device can view the same optical image as the user or surgeon, such as for example, an optical image from an endoscope.

SUMMARY OF THE INVENTION

This invention relates to a new and novel integrated beam splitter and adjustable light intensity control adapter for use primarily in the medical and surgical field. The adapter includes a housing having at least a first and second hollowed-out area, openings to receive an optical image from an optical device attached to the housing, an opening for an eyepiece and optics in the form of a beam splitter and a prism for producing two optical images of different intensities, one of which is directed through an eyepiece for a viewer to observe the optical image and a second through the optics to a recording means, such as a video camera. An adjustable light intensity means is provided, which may be manual or automatic, for controlling the intensity of the optical image received by the camera.

The adapter of the present invention overcomes several problems associated with the prior art devices. One advantage is that a single, compact, small, light weight housing includes all of the elements in an integrated assembly while providing relatively short focal length compared to the prior art devices with large diameter lens, which reduces light losses of optical images from optical devices used in medical and surgical applications while resulting in improved "F-Stop" based upon the ratio of the focal length of the lens to the lens diameter.

For example, an endoscope used in the medical profession produces a small optical image having relatively low level light intensity. Thus, any reduction in loss of light intensity becomes significant in that a minimum amount of light intensity is required to record an acceptable image by the video camera.

Another advantage of the present invention is that the video camera is mounted on and located on a planar surface of the housing in a position so as not to interfere with the viewer using the adapter.

Yet another advantage of the present invention is that an adjustable light intensity control means, such as an adjustable iris, can be used to select the required light intensity presented to the surface of the video camera.

BRIEF DESCRIPTION OF THE DRAWING

The foregoing and other advantages and features of the invention will be apparent from the following description of the preferred embodiment of the invention when considered together with the illustrations in the accompanying drawings and includes the following figures:

FIG. 1 is a perspective view of an adapter of the present invention having an optical device, eyepiece, and video camera attached thereto;

FIG. 2 is a pictorial representation of the optics of the adapter;

FIG. 3 is a top pictorial representation of an automatic iris adjusting system, including an iris drive motor and gear mechanism;

FIG. 4 is a front plan pictorial view of the relationship of a beam splitter relative to the iris drive motor;

FIG. 5 is a pictorial representation of the elements forming the adapter and the relative position of the elements relative to each other in the housing; and FIG. 6 is an isometric view of the adapter housing with the top cover removed and with a manually adjustable iris.

DESCRIPTION OF THE PREFERRED EMBODIMENT

An integrated beam splitter and adjustable iris adapter is shown generally as 12 in FIG. 1. The adapter includes a housing 14 which includes, in the interior thereof, a first hollowed-out area and a second hollowed-out area. The housing 14 includes means for defining a pair of axially aligned openings 16 and 18 which extend from the exterior of a surface of the housing 14 into the interior of the first hollowed-out area enclosed therein. The second hollowed-out area includes means for defining an aperture 120, shown in FIG. 6, which is adapted to receive a recording device, such as for example, a video camera 24.

A means, such as an adapter 26, is adapted to connect an optical device, such as for example, an endoscope 20 to the housing 14. The optical device, such as the endoscope 20, produces an optical image which is directed through opening 16, which is one of the pair of openings, and into the first hollowed-out area of the housing 14. The optical image is directed through and out the other opening 18 which is the other of the pair of openings. An eyepiece 28, is operatively coupled to the housing and positioned in an axial alignment with the pair of openings 16 and 18 to enable a viewer to observe the optical image from the optical device, such as for example, the endoscope 20.

In use, an optical image is generated by the optical device, such as the endoscope 20, is passed into the adapter 14 where the optical image is divided into two parts and an optical image having a light intensity which is less than half of the light intensity optical image, is passed directly through to the eye piece 28 over a first optical path and the remainder of the optical image is deflected along a path substantially perpendicular to the axis of the axially aligned pair of openings 16 and 18 along a second optical path to the recording device which, in the preferred embodiment, is a video camera 24.

FIG. 2 illustrates the optics of the adapter in greater detail. The optical image received from the optical device, such as the endoscope 20, traverses along a first optical path designated by arrow 40. A beam splitter 42 is adapted to intercept the optical image traversing the first optical path shown by arrow 40. The beam splitter is a typical beam splitter having a partially silvered front surface 44 which has silvered surface intensity such that less than half of the intensity of the optical image is passed by the beam splitter along the first optical path designated by line segment 46.

The remainder of the optical image is deflected by the silvered surface 44 along a second optical path shown generally as 50 having path segments 52, 54, 56 and 58. The portion of the optical image deflected by the silvered surface 44 of the beam splitter 42 is deflected substantially perpendicular to the first optical path 40, which optical path is in substantial axial alignment with the pair of openings 16 and 18, as illustrated in FIG. 1.

A prism 60 is positioned continuous to a beam splitter 42 and receives and deflects the remainder of the optical image from the beam splitter along the second optical path 50, as illustrated by light path segment 54.

In the preferred embodiment, a light intensity adjusting means, such as for example, adjustable iris 70, is positioned between the prism 60 and the end of the second optical path illustrated by line segment 58 for controlling the intensity of the optical image passing through the iris 70.

In the preferred embodiment, the recording device is a video camera 24. In FIG. 2, a lens 80 is illustrated to depict the lens into the recording device, such as for example, video camera 24. In use, a light intensity adjusting means is adapted to control the intensity of the optical image at the surface of the housing 14 which is the input to the recording device, such as for example, video camera 24.

FIG. 3 illustrates the construction of an automatically adjustable iris 70, which can be driven by a motor 82 through a gear train shown generally as 84. In use, the iris, or other light intensity adjusting means, can be manually adjusted or automatically adjusted by use of a servo loop to control the intensity of the optical image incident upon the input or imaging surface of the recording device through lens 80 in FIG. 2.

In the preferred embodiment of the present invention, the iris is controlled by a motor 82 through a gear train 84. In order to maintain the compactness of the device, the beam splitter/prism combination, illustrated as beam splitter 42 in FIG. 4, is positioned above the motor 82 and drive gear 84 which controls the setting of the iris 70.

FIG. 5 illustrates diagrammatically the relative location of the various elements to produce a small, integrated, compact integrated beam splitter and adjustable iris adapter. In the embodiment illustrated in FIG. 5, the beam splitter 42 and the prism 60 are positioned adjacent to each other to keep the length of the second optical path at the shortest possible distance. Thus, by positioning the beam splitter 42 and first prism 60 continuous to each other, the path traversed by the second optical path is maintained at the shortest possible distance for concurrently being deflected through an automatically adjustable iris 70 on to the surface of a lens 80. An iris drive motor 82 is adapted to be positioned substantially parallel to the second light path passing through the iris 70 such that the iris 70 can be automatically adjusted by the motor through a gear drive 84.

FIG. 6 illustrates in greater detail the mechanical structure and details of the housing and its associated members. The housing 14 includes a first hollowed-out area 100 which is located at one end of the housing 14. A top plate of the housing has been removed to show the interior construction of the housing 14. In construction, the first opening 18 for the eyepiece would be located in the cover and is not shown in FIG. 6, but is of the type of construction illustrated in FIG. 1. The opening 18 of the pair openings 16 and 18, illustrated in FIG. 1, is located on and extends from the exterior of the surface of a housing into the interior of the first hollowed-out area 100.

A second hollowed-out area 102 is located substantially perpendicular to and communicates with the first hollowed-out area 100. The second hollowed-out area has an aperture 120 which extends from the exterior of the second hollowed-out area 102 to the exterior of the housing 14. The aperture 120 is located on a surface which is substantially perpendicular to a surface having one of the two openings 16 or 18 therein.

In the preferred embodiment illustrated in FIG. 6, the iris 70 is adapted to be either adjusted manually or through an iris motor and gear assembly 84, as illustrated in FIG. 4. In such an embodiment, the housing 14 includes a third hollowed-out area 110 which is adapted to receive a motor and a fourth hollowed-out area 112 which is adapted to receive the iris drive mechanism 84 which may be any known drive mechanism, such as for example, a gear drive, pulley drive, friction drive, or the like. The lens 80, in lens holder 114, can be adjusted through opening 116.

The primary utility of the present invention is in the medical field where a surgeon can concurrently view a patient's body segment, subject of the operation, through known medical devices such as an endoscope, microscope, or other optical device which produces an optical image. Typically, the optical device is small and circular in shape.

When the image is recorded on a video camera, only a small portion of the video frame is filled with the image. Thus, the intensity of the optical image presented to a video camera recording means can be controlled to compensate for different images of different optical intensities from different optical devices. Thus, the adapter of the present invention has utility in any application where an optical image is to be received and viewed by two users or one user and a recording means. In the broadest aspect the recording means could be a second viewer.

What is claimed is:

1. An integrated beam splitter and adjustable light intensity control adapter comprising
a housing including a first hollowed-out area located at one end thereof and a pair of axially aligned openings, one of which extends from the exterior of a surface of the housing into the interior of said first hollowed-out area and the other of said opening extending from the interior of said first hollowed-out area to the exterior of an opposed surface of the housing, said housing including a second hollowed-out area which is located substantially perpendicular to and which communicates with said first hollowed-out area, said second hollowed-out area having an aperture which extends from the interior of said second hollowed-out area to the exterior of a planar surface of said housing, which planar surface is substantially perpendicular to said surface and said opposed surface having one of said pair of openings;

means operatively connected to said housing for attaching an optical device, which is adapted to produce an optical image to the housing wherein a said optical image is directed through said one of said pair of openings and into said first hollowed-out area and out through the other of said pair of openings;

viewing means operatively coupled to said housing and positioned in axial alignment with said other one opening of said pair of openings to enable a viewer to observe a said optical image from a said optical device;

a beam splitter positioned within said first hollowed-out area and between said pair of openings to receive through said one opening said optical image and for passing a portion of a said optical image at a light intensity which is less than one-half of the intensity of a said optical image through a first optical path including said other opening and through said viewing means and for deflecting the remainder of said optical image through a second optical path substantially perpendicular to the axis of said axially aligned pair of openings;

a prism positioned within said first hollowed-out area and adjacent said beam splitter and along said second optical path to receive and deflect the remainder of a said optical image from said beam splitter into said second hollowed-out area and through said aperture;

light intensity adjusting means positioned in said second hollowed-out area and along said second optical path between said prism and aperture for controlling the intensity of that portion of a said optical image at the planar surface of the housing; and means including a lens operatively coupled to said housing on said planar surface at said aperture for coupling a recording means to said second hollowed-out area along said second optical path to record a said optical image having a controlled intensity.

2. The integrated beam splitter and adjustable light intensity control adapter of claim 1 wherein said light intensity adjusting means is an adjustable iris.

3. The integrated beam splitter and adjustable light intensity control adapter of claim 2 wherein said housing includes a third hollowed-out area located adjacent said second hollowed-out area with the axis thereof substantially perpendicular to the axis of said first hollowed-out area and means defining a passageway between said second hollowed-out area and said third hollowed-out area and further comprising an iris drive motor located in said third hollowed-out area.

4. The integrated beam splitter and adjustable light intensity control adapter of claim 3 wherein said housing further comprises a fourth hollowed-out area located contiguous said third hollowed-out area; and an iris drive mechanism operatively coupled to the adjustable iris and to said iris drive motor, said iris drive motor being responsive to a control signal for driving said adjustable iris through said gear drive mechanism in at least one of a clockwise and counterclockwise direction in response to a control signal.

5. The integrated beam splitter and adjustable light intensity control adapter of claim 1 further comprising a video camera operatively coupled to said housing by said recording means coupling means for producing a video information signal of a said optical image produced by a said optical device.

6. The integrated beam splitter and adjustable light intensity control adapter of claim 1 further comprising an endoscope operatively coupled to said housing by said optical device attaching means for producing an optical image to be recorded by a recording means.

7. The integrated beam splitter and adjustable light intensity control adapter of claim 4 wherein said adjustable iris includes an adjustable iris mechanism which is adapted to cooperate with said iris drive mechanism to rotate said adjustable iris.

8. The integrated beam splitter and adjustable light intensity control adapter of claim 4 wherein said housing includes an adjustment opening extending from the interior of said fourth hollowed-out area to the exterior of said housing, said adjustment opening being located at a position to enable a user to manually adjust said adjustable iris to control the light intensity of a said optical image at said aperture.

9. The integrated beam splitter and adjustable light intensity control adapter of claim 2 wherein said viewing means is an eyepiece.

10. An integrated beam splitter and adjustable light intensity control adapter for use with a video camera and an optical device which produces an optical image which is to be recorded by said video camera, said adapter comprising housing means including a first hollowed-out area and a second hollowed-out area located substantially perpendicular to said first hollowed-out area, said second hollowed-out area communicating with said first hollowed-out area at one end thereof, said housing including means for defining a pair of axially aligned openings which extend from the exterior of said housing into the interior of said first hollowed-out area, said housing including means for defining an aperture which extends from the interior of the second hollowed-out area to the exterior of the housing such that the aperture is located on a housing service which is substantially perpendicular to said pair of aligned openings;

means operatively connected to said housing for attaching an optical device, which is adapted to produce an optical image, to the housing wherein a said optical image is directed through said one of said pair of openings and into said first hollowed-out area and out through the other of said pair of openings;

an eyepiece operatively coupled to said housing and positioned in axial alignment with said other one opening of said pair of openings to enable a viewer to observe a said optical image from a said optical device;

a beam splitter positioned within said first hollowed-out area and between said pair of openings to receive through said one opening said optical image and for passing a portion of a said optical image at a light intensity which is less than one-half of the intensity of a said optical image through a first optical path including said other opening and through said eyepiece and for deflecting the remainder of said optical image through a second optical path substantially perpendicular to the axis of said axially aligned pair of openings;

a prism positioned within said first hollowed-out area and adjacent said beam splitter along said second optical path to receive and deflect the remainder of said optical image from said beam splitter into said second hollowed-out area and through said aperture;

a variable iris positioned in said second hollowed-out area and along said second optical path between said prism and said aperture for selectively controlling the intensity of that portion of a said optical image at the planar surface of the housing; and means including a lens for operatively coupling a said video camera on said planar surface at said aperture to position the lens along said second optical path to record a said optical image having a controlled intensity at the imaging surface of a said video camera.

11. The integrated beam splitter and adjustable light intensity control adapter of claim 10 wherein said housing includes a third hollowed-out area located adjacent said second hollowed-out area with the axis thereof substantially perpendicular to the axis of said first hollowed-out area and the axis of said third hollowed-out area and further comprising an iris drive motor located in said third hollowed-out area.

12. The integrated beam splitter and adjustable light intensity control adapter of claim 11 wherein said housing further comprises a fourth hollowed-out area located contiguous said third hollowed-out area; and an iris drive mechanism coupled to the adjustable iris and to said iris drive motor, said iris drive motor being responsive to a control signal for driving said adjustable iris through said iris drive mechanism in at least one of a clockwise and counterclockwise direction in response to a said control signal.

* * * * *